(12) United States Patent
Quake et al.

(10) Patent No.: US 6,947,846 B2
(45) Date of Patent: Sep. 20, 2005

(54) NON-METRIC TOOL FOR PREDICTING GENE RELATIONSHIPS FROM EXPRESSION DATA

(75) Inventors: Stephen R. Quake, San Marino, CA (US); R. Michael van Dam, Pasadena, CA (US); James P. Brody, San Clemente, CA (US); Rebecca Shafee, Cambridge, MA (US)

(73) Assignee: California Institute of Technology, Pasadena, CA (US)

( * ) Notice: Subject to any disclaimer, the term of this patent is extended or adjusted under 35 U.S.C. 154(b) by 101 days.

(21) Appl. No.: 10/289,141

(22) Filed: Nov. 5, 2002

(65) Prior Publication Data

US 2003/0152969 A1 Aug. 14, 2003

Related U.S. Application Data

(60) Provisional application No. 60/338,745, filed on Nov. 5, 2001.

(51) Int. Cl.[7] .............................................. G06F 17/00
(52) U.S. Cl. ............................... 702/20; 702/19; 435/6
(58) Field of Search ............................... 435/6; 436/63, 436/84; 702/19, 20

(56) References Cited

PUBLICATIONS

Alizadeh et al., (2000). "Distinct types of diffuse large B–cell lymphoma identified by gene expression profiling," *Nature*, 403:503–511.

Butte et al., (2000). "Mutual Information Relevance Networks: Functional Genomic Clustering Using Pairwise Entropy Measurements," *Pacific Symposium on Biocomputing 2000*, pp. 418–429, conference held in Hawaii.

Butte et al., (2000). "Discovering functional relationships between RNA expression and chemotherapeutic susceptibility using relevance networks," *PNAS*, 97(22):12182–12186.

Butte, A., "Advantages of relevance networks over other bioinformatics analysis tools in functional genomics," downloaded from http://www.xpogem.com/Xpogen_Relevance_Network.pdf on Oct. 25, 2001.

Detweiler et al., (2001). "Host microarray analysis reveals a role for the Salmonella response regulator phoP in human macrophage cell death," *PNAS*, 98(10):5850–5855.

Iyer et al., (1999) "The transcriptional program in the response of human fibroblasts to serum," *Science*, 283(5398):83–87.

Liang et al., (1998). "Reveal, A General Reverse Engineering Algorithm for Interference of Genetic Network Architectures," *Pacific Symposium on Biocomputing*, 3:18–29.

Perou et al., (1999). "Distinctive gene expression patterns in human mammary epithelial cells and breast cancers," *PNAS*, 96(16):9212–9217.

Perou et al., (2000). "Molecular portraits of human breast tumors," *Nature*, 406:747–752.

Ross et al., (2000). "Systematic variation in gene expression patterns in human cancer cell lines," *Nature Genetics*, 24:227–235.

Walker et al., (1999). "Prediction of Gene Function by Genome–Scale Expression Analysis: Prostate Cancer–Associated Genes," *Genome Research*, 9(12):1198–1203.

Walker et al., (1999). "Pharmaceutical target discovery using Guilt–by–Association: schizophrenia and Parkinson's disease genes," *Proc. of Int. Conf. on Intelligent Systems for Mol. Biol.*, 146:282–286.

Walker, M.G., "Drug Target Discovery by Gene Expression analysis: Cell Cycle Genes," *Current Cancer Drug Targets*, 1(1), downloaded from http://www.bentham.org/ccdt1–1/walker/walker_c.htm on Oct. 25, 2001.

*Primary Examiner*—James Martinell
(74) *Attorney, Agent, or Firm*—Townsend and Townsend and Crew LLP (57) ABSTRACT

Techniques for processing gene expression data and predicting gene relationships are provided. More specifically, a method for processing gene expression ratios may include discretizing a first expression ratio for a first gene and a second expression ratio for a second gene for each of a plurality of experiments into one of three indications, calculating the probability that the combination of the discretized expression ratios for each of the plurality of experiments arises by random chance, and determining whether the first gene and the second gene are related.

23 Claims, 5 Drawing Sheets

NON-METRIC TOOL FOR PREDICTING GENE RELATIONSHIPS FROM EXPRESSION DATA

CROSS-REFERENCES TO RELATED APPLICATIONS

This application claims priority to U.S. Provisional No. 60/338,745 filed Nov. 5, 2001, which is incorporated by reference herein.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

COPYRIGHT NOTICE

A portion of this application contains computer codes, which are owned by California Institute of Technology. All rights have been preserved under the copyright protection, California Institute of Technology ©2002.

BACKGROUND OF THE INVENTION

The present invention is related to techniques for processing gene expression data and predicting gene relationships.

Since ancient time, humans have been searching for early diagnosis and effective treatment of diseases. In the last several hundred years, medical techniques, including blood sample analysis and physical imaging analysis, greatly improved the ability for diagnosis and treatment. But no cure has yet been found for many deadly and debilitating diseases, including cancer. To further improve humans' physical health, gene diagnosis and gene therapy have been proposed and experimented. The human genome sequencing has been largely completed and the focus of medical research has been shifted to unveiling functions of various genes and their relations.

Relationship of genes may be inferred from their expression data, and may be organized in various forms, including clustering, dendrogram, and relevance network. Under the clustering method, genes are grouped into clusters based on their proximity in a multi-dimensional expression space, as measured by, among others, Euclidean distance, linear correlation, and non-linear correlation. Consequently, all genes are organized into a hierarchical structure. In contrast, under the dendrogram method, genes are comprehensively compared with a metric, and then added to a binary tree in order of decreasing correlation such that pairs with the highest correlation are closest in the tree. Both the clustering method and the dendrogram method suffers from several drawbacks. First, the clustering method based on Euclidean distance cannot handle genes with missing data, because incomplete expression vectors for these genes cannot be accurately oriented in the multi-dimensional space. Second, the dendrogram method and the clustering method based on Euclidean distance cannot identify negatively correlated genes and therefore ignore some important biological relations. Third, many clustering methods do not allow genes to belong to multiple clusters, and thus cannot accurately describe genes that are under the control of two or more different regulatory factors. Similarly, the dendrogram method has the same problem.

Under the relevance network method, a probability function, such as that based on mutual information or combinatorics, is used to estimate the probability that genes are independent. If the probability is low, the genes are predicted as having significant relation. Consequently, they are placed as connected in distinct gene networks with varying number of elements. Unlike the dendrogram method and many clustering methods, the relevance network method incorporates only genes with significant relations. In addition, a probability function is non-metric, so that the probability that two genes are related does not need to satisfy the "triangle inequality." Under the "triangle inequality," the distance, such as Euclidean distance, between genes A and B cannot exceed the sum of distance between genes A and C and distance between genes B and C. This requirement limits the ability of the metric method to describe gene relationships. Genes A and B may be weakly related or unrelated, even though both genes are regulated in part by the same gene C. Hence distance between genes A and C and distance between genes B and C may be small, while distance between genes A and B is large, exceeding the sum of distance between genes A and C and distance between genes B and C. Such relationships among genes A, B, and C cannot be adequately described by the metric method, but a non-metric method such as the relevance network using a probability function can provide an adequate description.

Some relevance network methods utilize a 2×2 matrix to calculate the probability that genes are independent, as exemplified in Walker, M. G. et al., Prediction of Gene Function by Genome-Scale Expression Analysis: Prostate Cancer-Associated Genes, *Genome Research* 9(12): 1198–1203, 1999, Walker, M. G. et al., Pharmaceutical Target Discovery Using Guilt-by-Association: Schizophrenia and Parkinson's Disease Genes, *Proceedings of the International Conference on Intelligent Systems for Molecular Biology* 146: 282–286, 1999, and Walker, M. G., Drug Target Discovery by Gene Expression Analysis: Cell Cycle Genes, *Current Cancer Drug Targets* 1(1), 2001. These methods use binary expression data representing presence or absence of genes in a particular cell sample, and analyze gene relations based on presence or absence of genes in a common set of cell samples. These methods do not study continuous expression data representing regulatory effect of genes, but these data contain important information on gene relations.

As an improvement, Liang proposed a relevance network method that discretizes continuous gene expression data into binary states, i.e., on or off states of regulatory effect, as described in Liang S., Reveal, A General Reverse Engineering Algorithm for Inference of Genetic Network Architectures, *Pacific Symposium on Biocomputing* 3:18–29 (1998). This method uses the binary representation for genes, which does not fully represent richness of expression data. Expression data may show that genes are up regulated, down regulated, or unchanged.

In contrast, Butte et al. used a relevance network method that discretizes the continuous expression data representing gene regulatory effect into n sub-ranges, e.g., 10 sub-ranges, as described in Butte A. J. el al., Mutual Information Relevance Networks: Functional Genomic Clustering Using Pairwise Entropy Measurements, in Altman, R., Dunker, K., Hunter L., Lauderdale K., Klein T. eds., *Pacific Symposium on Biocomputing*, at 418–429, (2000), Hawaii, World Scientific. This method uses narrow sub-ranges; therefore it cannot effectively filter out measurement noises that are associated with gene expression data, and may yield inaccurate gene correlation.

BRIEF SUMMARY OF THE INVENTION

According to the present invention, techniques for processing gene expression data and predicting gene relationships are provided. Merely by way of example, a method for predicting gene relationships may include providing a control sample and a plurality of experimental samples, and performing one experiment on each of the plurality of experimental samples. In addition, the method measures a first gene control signal corresponding to a first gene from the control sample, and measures a first gene experimental signal corresponding to the first gene from each of the plurality of experimental samples. Further, the method calculates a first expression ratio corresponding to the first gene for each of the plurality of experimental samples and discretizes the first expression ratio for each of the plurality of experimental samples into one of three indications representing the first gene up-regulated, not changed, or down-regulated. Similarly, the method repeats the above measurements and analyses for a second gene to obtain a discretized second expression ratio for each of the plurality of experimental samples. Based on the discretized expression ratios for the first gene and the second gene, the method calculates the probability that the combination of the discretized expression ratios for each of the plurality of experimental samples arises by random chance. Finally, the method determines whether the first gene and the second gene are related.

In another embodiment, a method for processing gene expression ratios may include gathering gene expression ratio data from a database. The gene expression data comprises a first expression ratio for a first gene for each of a plurality of experiments and a second expression ratio for a second gene for each of the plurality of experiments. The method discretizes the first expression ratio for each of the plurality of experiments into one of three indications, the three indications representing the first gene up-regulated, not changed, or down-regulated, and similarly discretizes the second expression ratio for each of the plurality of experiments. Based on the discretized expression ratios, the method calculates the probability that the combination of the discretized expression ratios for each of the plurality of experiments arises by random chance. Further, the method determines whether the first gene and the second gene are related.

In yet another embodiment, a method for processing gene expression ratios may include gathering a first plurality of gene expression data for a first plurality of experiments with a first control sample and calculating a first probability in response to the first plurality of gene expression data that a pair genes are related. In addition, the method includes gathering a second plurality of gene expression data for a second plurality of experiments with a second control sample and calculating a second probability in response to the second plurality of gene expression data that said pair genes are related. Further, the method includes calculating a combined probability in response to the first probability and the second probability, and determining whether said pair of genes are related.

In yet another embodiment of the present invention, a method for processing gene expression ratios includes gathering gene expression data. The gene expression data include a first gene control signal and a first gene experimental signal for a first gene for each of a plurality of experiments, and a second gene control signal and a second gene experimental signal for a second gene for each of the plurality of experiments. In addition, the method includes discretizing the first expression ratio for each of the plurality of experiments into one of three indications, the three indications representing the first gene up-regulated, not changed, or down-regulated, and discretizing the second expression ratio for each of the plurality of experiments into one of three indications, the three indications representing the second gene up-regulated, not changed, or down-regulated. Moreover, the method includes calculating the probability that the combination of the discretized first expression ratio for each of the plurality of experiments and the discretized second expression ratio for each of the plurality of experiments arises by random chance. Further, the method includes determining whether the first gene and the second gene are related.

In yet another embodiment of the present invention, a computer-readable medium including instructions for processing gene expression ratios includes one or more instructions for gathering gene expression data. The gene expression data comprises a first expression ratio for a first gene for each of a plurality of experiments and a second expression ratio for a second gene for each of the plurality of experiments. Moreover, the computer-readable medium includes one or more instructions for discretizing the first expression ratio for each of the plurality of experiments into one of three indications, the three indications representing the first gene up-regulated, not changed, or down-regulated. Similarly, the computer-readable medium also includes one or more instructions for discretizing the second expression ratio. Further, the computer-readable medium includes one or more instructions for calculating the probability that the combination of the discretized first expression ratio for each of the plurality of experiments and the discretized second expression ratio for each of the plurality of experiments arises by random chance. In addition, the computer-readable medium includes one or more instructions for determining whether the first gene and the second gene are related.

DETAILED DESCRIPTION OF THE INVENTION

According to the present invention, techniques for predicting gene relationships and processing gene expression data are provided.

Figure 1:
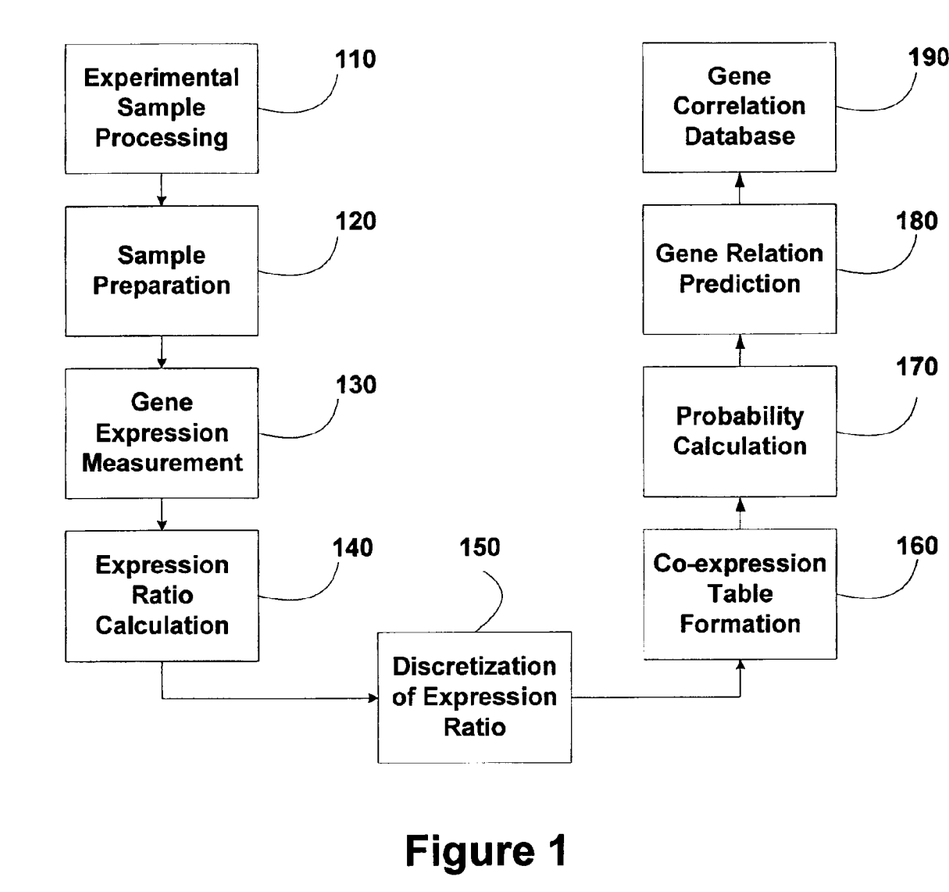
FIG. 1 is a block diagram of various steps for predicting gene relationships based on gene expression data according to an embodiment of the present invention.

FIG. 1 is a block diagram for predicting gene relationships according to an embodiment of the present invention. The method includes eight steps: experimental sample processing step 110, sample preparation step 120, gene expression measurement step 130, expression ratio calculation step 140, discretization of expression ratio step 150, co-expression table formation step 160, probability calculation step 170, gene relation prediction step 180, and gene correlation database step 190.

Figure 2:
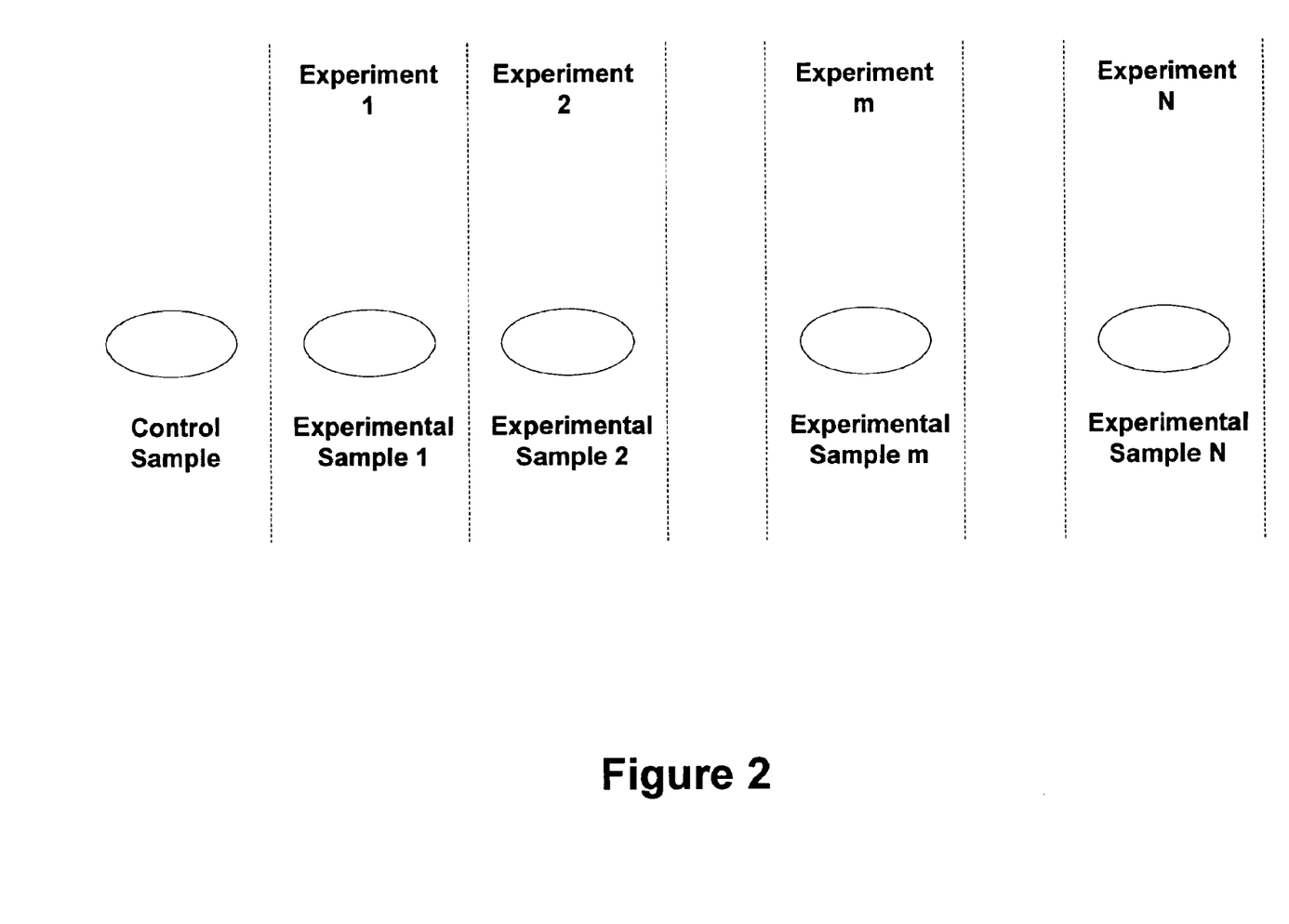
FIG. 2 illustrates a control cell sample and n experimental cell samples.

At experimental sample processing step 110, experimental samples are processed in various studies. In each study, a control sample and N experimental samples are provided as shown in FIG. 2. The control sample preferably has a cell type similar to those of experimental samples. Subsequently, the experimental samples are processed under various experimental conditions. For instance, experimental sample 1 undergoes experiment 1, experimental sample 2 undergoes experiment 2, . . . , experimental sample m undergoes experiment m, . . . , and experimental sample N undergoes experiment N. Experiments 1 through N may be performed under the same or different experimental conditions.

Figure 3:
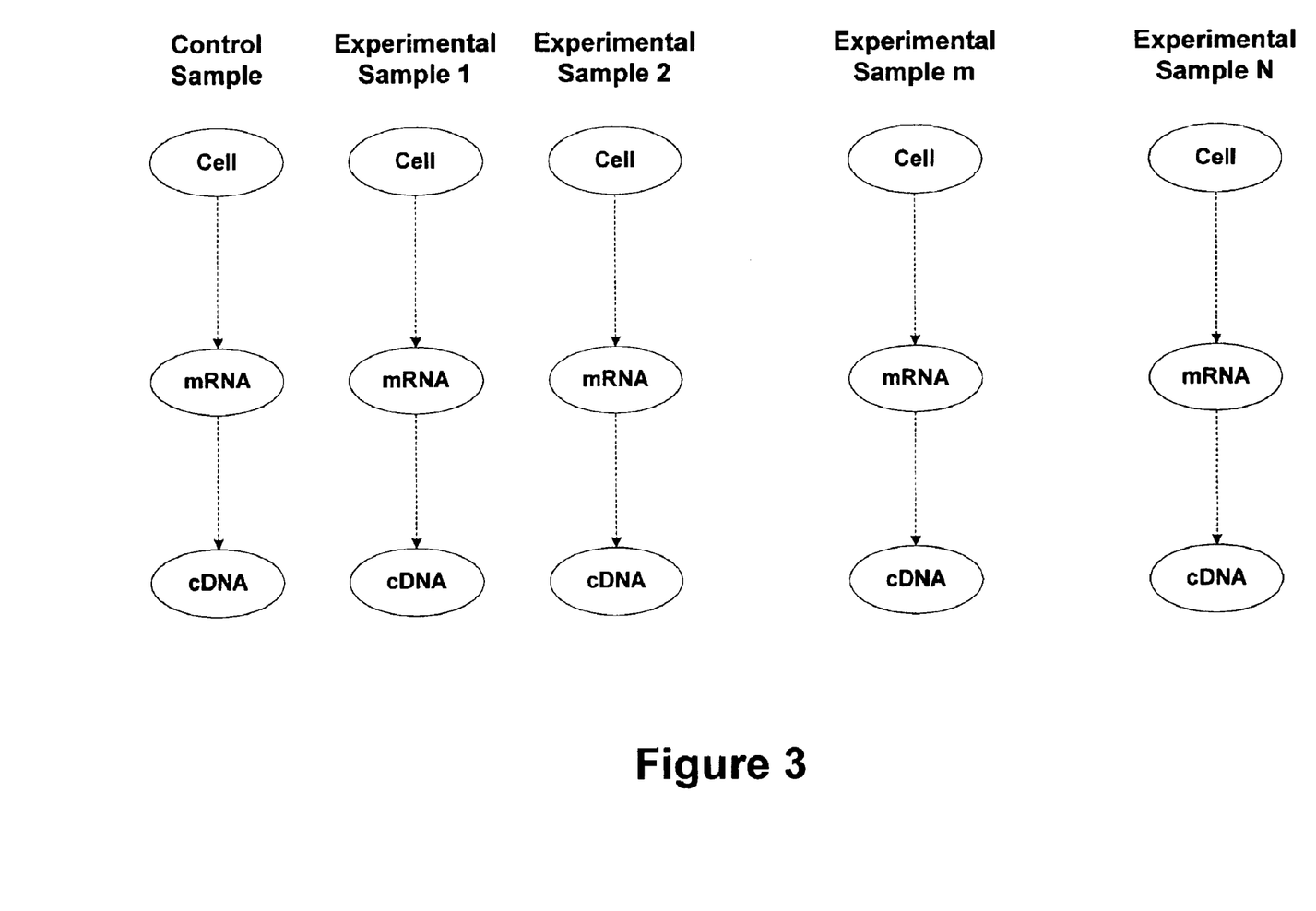
FIG. 3 illustrates extraction of mRNA and reverse transcription of cDNA from control cell sample and experimental cell samples.

Next, at sample preparation step 120, the control sample and the N experimental samples are prepared for gene expression measurement. For example, as shown in FIG. 3, the messenger RNA (mRNA) is isolated from the control sample and the N experimental samples, and subsequently converted to the reverse complementary DNA (cDNA) through reverse transcription. To allow comparison, the cDNA for the control sample and the experimental samples are labeled either directly with different flurochromes or indirectly with different epitopes. Alternatively, other detection schemes for cDNA may be employed, such as radioisotopes, electronic detection, or electrochemical detection. In addition, mRNA may be measured without conversion to cDNA. For example, mRNA may be directly measured at sample preparation step 120.

Figure 4:
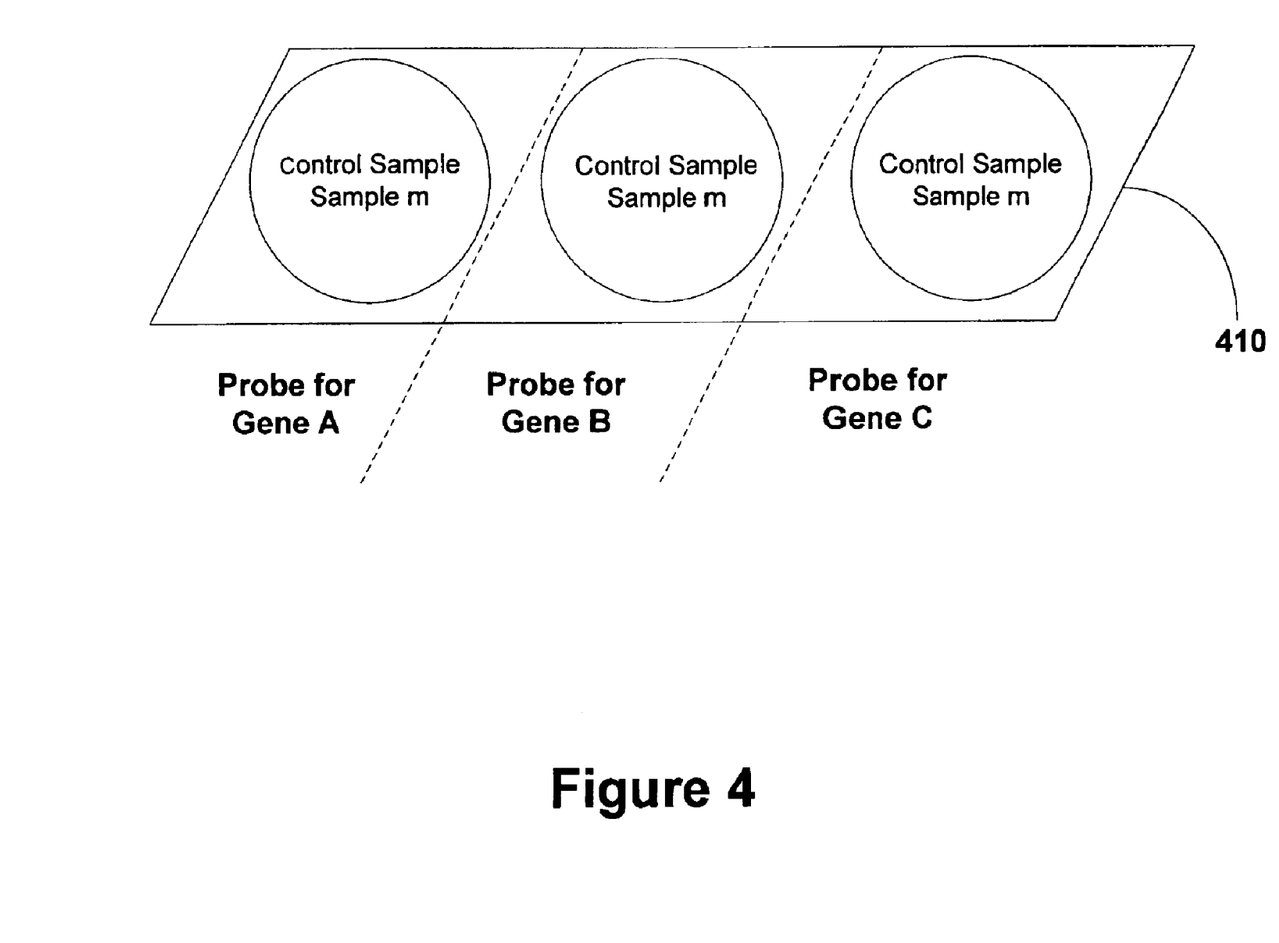
FIG. 4 illustrates measurement of gene expression data with microarray technology.

Subsequently, at the gene expression measurement step 130, the cDNAs for the control sample and the experimental samples are applied to a microarray, which contains DNA probes for genes. For example, as shown in FIG. 4, there are DNA probes for genes A, B, and C on a microarray 410. If a cDNA sample possesses a nucleotide sequence complementary to that of a DNA probe, hybridization would occur. Upon hybridization, the fluorescent intensities at each spot of the microarray may be measured with a scanning system. Consequently, for each gene and for each experiment, the expression ratio r may be calculated in various means. For example, $$r = \log_2\left(\frac{\text{Signal}_{experiment} - \text{Background}_{experiment}}{\text{Signal}_{control} - \text{Background}_{control}}\right) \quad \text{(Equation 1)}$$

where $\text{Signal}_{experiment}$ is the fluorescent intensity for a gene, corresponding an experimental sample, and $\text{Signal}_{control}$ is the fluorescent intensity for the control sample corresponding to the same gene. $\text{Background}_{experiment}$ and $\text{Background}_{control}$ are fluorescent intensities resulting from variability in overall fluorescence intensity and pixel intensity, with respect to experimental sample and control sample respectively.

Afterwards, at the discretization of expression ratio step 150, the expression ratio r is discretized into three states: the gene up regulated, not changed, and down regulated during the corresponding experiment. As shown in Table 1, if r is larger than a noise threshold $T_H$, the gene was up regulated and is assigned a value of "+." If r is larger than or equal to $T_L$ and is smaller than or equal to $T_H$, the gene was not changed and is assigned a value of 0. If r is smaller than $T_L$, the gene was down regulated and is assigned a value of "−."

The noise thresholds $T_H$ and $T_L$ are used to filter out measurement errors associated with the experimental sample processing step 110, the sample preparation step 120, the gene expression measurement step 130, and the expression ratio calculation step 140. Even if a gene in an experiment sample has not changed in the corresponding experiment, the expression ratio r may not equal zero because $\text{Signal}_{experiment}$−$\text{Background}_{experiment}$ may not equal $\text{Signal}_{control}$−$\text{Background}_{control}$. For example, the different signal strength for the experiment sample and the control sample for the unchanged gene may result from property variations of the experiment sample and the control sample even if the two samples are of the same cell type. In addition, the microarray measurements may introduce noises related to fluorescent excitation and emission. Moreover, measurement noises for up-regulation and for down-regulation may be different, so magnitudes of $T_H$ and $T_L$ may differ. Furthermore, up-regulation and down-regulation of genes may be determined by other means even without computing an expression ratio.

TABLE 1

Discretization of Expression Ratio

| Expression Ratio | Discretized State | Discretized Value |
|---|---|---|
| r > $T_H$ | up-regulated | + |
| $T_L \leq r \leq T_H$ | not changed | 0 |
| r < $T_L$ | down-regulated | − |

Next, the discretized expression ratios for various experiments and for various genes are organized into a summary table. As exemplified in Table 2, discretized expression ratios for ten experimental samples and three genes A, B, and C are tabulated. "X" indicates that the expression ratio is not available for the corresponding experiment and the corresponding gene. Unavailability of expression ratio may result from reasons such as lack of gene measurement on microarray or poor quality of measurement data. For example, for experimental sample #1, both genes A and B are up-regulated, but the expression ratio for gene C is not available.

TABLE 2

Gene Expression Ratio Summary

| | Experiment | | | | | | | | | |
|---|---|---|---|---|---|---|---|---|---|---|
| Gene | #1 | #2 | #3 | #4 | #5 | #6 | #7 | #8 | #9 | #10 |
| A | + | 0 | 0 | − | + | 0 | + | + | X | X |
| B | + | + | 0 | − | + | − | + | 0 | X | X |
| C | X | X | − | + | 0 | 0 | 0 | + | − | 0 |

Next, at the co-expression table formation step 160, a co-expression table for a pair of genes is obtained based on an expression ratio summary table. Any experiment that does not provide a gene expression ratio for both genes is ignored. For example, table 3, as derived from table 2, shows numbers of occurrences that genes A and B have various combinations. In three experiments, both genes A and B were both up regulated, in one experiment, gene A was up regulated while gene B was not changed, and in no experiment, gene A was up regulated and gene B was down regulated. Therefore, the total number of experiments in which gene B was up regulated is 4.

TABLE 3

Co-expression Table for Genes A and B

| Gene A | Gene B | | | |
|---|---|---|---|---|
| | + | 0 | − | Total |
| + | (++) = 3 | (+0) = 1 | (+−) = 0 | (+total) = 4 |
| 0 | (0+) = 1 | (00) = 1 | (0−) = 1 | (0 total) = 3 |
| − | (−+) = 0 | (−0) = 0 | (−−) = 1 | (−total) = 1 |
| Total | (total +) = 4 | (total 0) = 2 | (total −) = 2 | (total total) = 8 |

Given a co-expression table for a pair genes, there is the probability that the two genes are unrelated in their respective up-regulation, down-regulation, and no change in the same experiments. At the probability calculation step 170, such probability P can be estimated with the Fisher Exact test, as described in Mehta, C. R., Patel, N. R. Algorithm 643, FEXACT: A FOTRAN Subroutine for Fisher's Exact Test on Unordered rxc Contingency Tables. ACM Transactions on Mathematical Software: 12(2), at 154–161 (June 1986), and in Clarkson, D. B., Fan, Y-A., and Joe, H. A Remark on Algorithm 643: FEXACT: An Algorithm for Performing Fisher's Exact Test in rxc Contingency Tables. ACM Transactions on Mathematical Software: 19(4), at 484–488 (December 1993). Alternatively, probability P may be calculated with approximated Fisher Exact test as described below.

$$P_{A,B} = \frac{(+total)!(0total)!(-total)!(total+)!(total0)!(total-)!}{(totaltotal)!(++)!(+0)!(+-)!(0+)!(00)!(0-)!(-+)!(-0)!(--)!} \quad \text{(Equation 2)}$$

The approximated Fisher Exact test requires less computation than the Fisher Exact test and hence improves performance of data processing. The magnitude of the probability P can be effectively represented with its base 10 logarithm p, as shown in equation 3.

$$p_{A,B} = \log P_{A,B} \quad \text{(Equation 3)}$$

Next at the gene relation prediction step 180, the relatedness of two genes are assessed. If $p_{A,B}$ is smaller than a correlation factor, it is unlikely that the up-regulation, down-regulation, and no change of the two genes are unrelated; therefore the pair of genes are significantly related. If $p_{A,B}$ is larger than or equal to the correlation factor, the pair of genes are not significantly related. The magnitude of correlation factor may depend on sample sizes, number of experiments, acceptable rates of false correlations, and other factors. For example, the correlation factor may be set larger than −8 but smaller than −2. When the correlation factor equals −8, few false correlations may be incorporated but some true correlations may be missed. In contrast, when the correlation factor equals −2, some false correlations may be incorporated but few true correlations may be missed. As exemplified in tables 2 and 3, the pair of genes may be genes A and B, genes A and C, and genes B and C.

Next, at the gene correlation database step 190, the predicted gene relationships are summarized and form a gene correlation database, from which all genes significantly related to a given gene may be obtained. Such database may improve ease of access to the predicted gene relations, but is nonetheless optional to practice the present invention.

According to another embodiment of the present invention, gene relationship may be predicted based on gene expression data measured from experiments with different control samples. As shown in FIGS. 2–4, $p_{A,B}$ may be calculated from gene expression data measured from experiments with the same control sample. But many experiments are performed with different control samples, so $p_{A,B}$ values corresponding to different control samples may be combined to yield combined $p_{A,B(combined)}$ to take full advantage of available experimental data. $p_{A,B(combined)}$ may be calculated in various ways, such as Fisher combined p-value. Fisher combined p-value first calculates $\chi^2$ and degree of freedom ("DOF"), as follows:

$$\chi^2 = -2\sum_{i=1}^{G} \ln p_{A,B,i} \quad \text{(Equation 4)}$$

$$\text{DOF} = 2G \quad \text{(Equation 5)}$$

Where G is number of experimental groups and $p_{A,B,i}$ is $p_{A,B}$ for experimental group i. Different experimental groups have different control samples, whereas different experiments within the same experimental group have the same control sample. Next, Fisher combined p-value uses $\chi^2$ and DOF to calculate $p_{A,B(combined)}$. Alternatively, other methods may be used to calculate $p_{A,B(combined)}$. $p_{A,B(combined)}$ may be determined by analyzing reliability of $p_{A,B,i}$ for each experimental group. For example, the smallest $p_{A,B,i}$ among all experimental groups may be adopted as $p_{A,B(combined)}$. After $p_{A,B(combined)}$ is obtained, the relatedness of two genes are assessed. As described above, if $p_{A,B(combined)}$ is smaller than a correlation factor, it is unlikely that the up-regulation, down-regulation, and no change of the two genes are unrelated; therefore the pair of genes are significantly related. If $p_{A,B(combined)}$ is larger than or equal to the correlation factor, the pair of genes are not significantly related.

Figure 5:
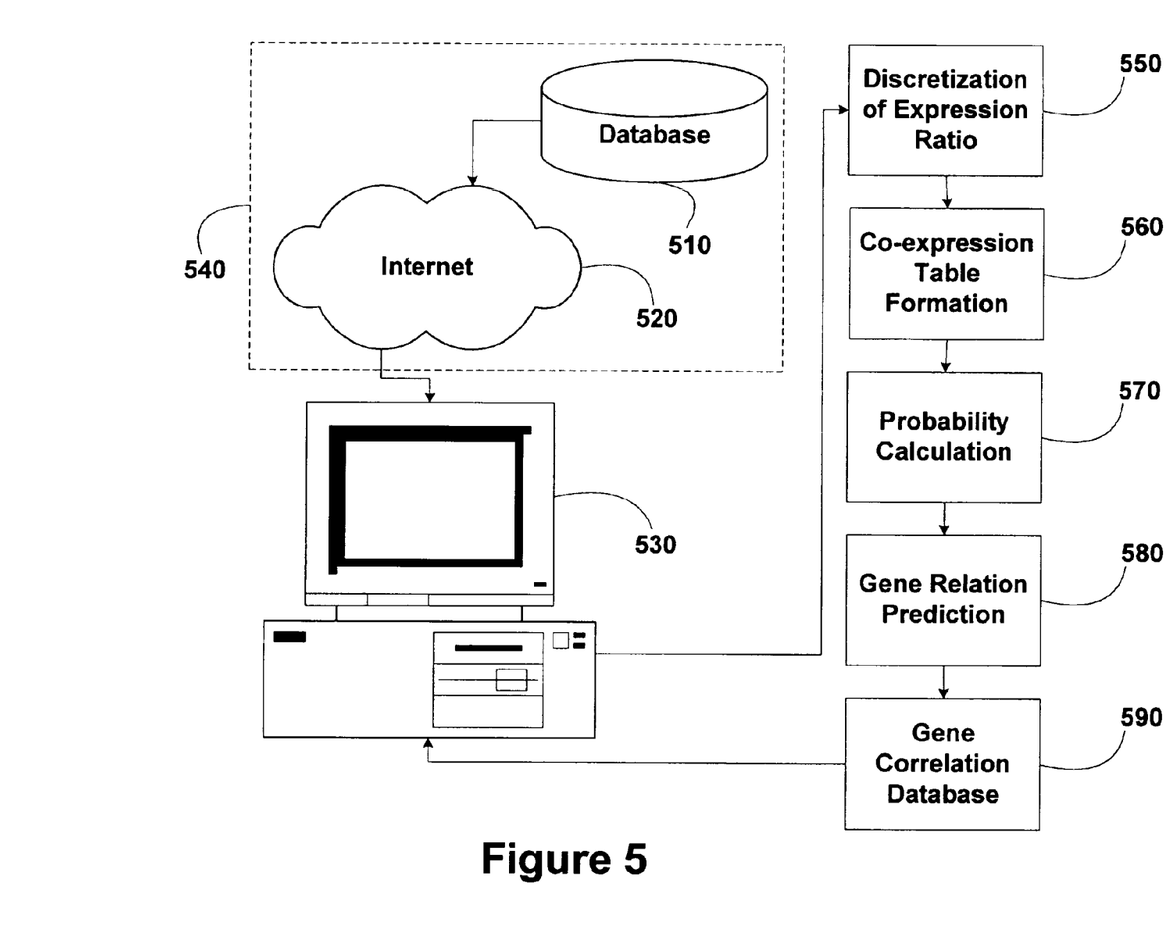
FIG. 5 is a block diagram of various steps for processing gene expression ratio between experimental sample and control sample.

FIG. 5 illustrates a block diagram according to yet another embodiment of the present invention. The method includes six steps: data gathering step 540, discretization of expression ratio step 550, co-expression table formation step 560, probability calculation step 570, gene relation prediction step 580, and gene relation database formation step 590.

At the data gathering step 540, a computer 530 gathers gene expression ratio data for one or several genes from a database 510 or other sources such as a data file or spreadsheet. The data may be transferred through the Internet 520 or by other means such as DVD, CD, floppy diskette, data printed on paper, or other media. The gene expression ratios may have been obtained from one or several experiments under one or several studies. Next the expression ratios are discretized in the step 550 and tabulated in the step 560, substantially similar to the steps 150 and 160 as discussed above. Consequently, the probability for a pair of genes to be unrelated is calculated and the relationship between the genes are assessed in the steps 570 and 580, substantially similar to the steps 170 and 180 as discussed above. Finally, at the gene correlation database step 590, the predicted gene relationships are summarized and form a gene correlation database, from which all genes significantly related to a given gene may be obtained. The gene correlation database may be stored on the computer 530 or another computer connected to the computer 530 over a network such as the Internet. The gene correlation database would improve ease of access to predicted gene relationships, but the step 590 is nonetheless optional for practicing the present invention.

To prove the principle and operation of the invention, we performed prediction of gene relationships for various genes. Prediction of relationships includes data gathering, discretization of expression ratio, co-expression table formation, probability calculation, gene relation prediction, and gene relation database formation. Embodiments of the present invention include code that directs a processor to perform the inventive steps as discussed above. An exemplary computer code has been implemented using Pentium PC and C++ computer language. This computer code is not intended to limit the scope of the claims herein. One of ordinary skill in the art would recognize other variations, modifications, and alternatives.

Part of the computer code is reproduced below. The computer code has three major components:

Declarations, initializations, and parsing command line;

Establishing connection with database and importing discretized expression ratios;

Computing p-values for gene pairs and write output file.

Declarations, Initializations, and Parsing Command Line

In this section, the computer code directs the processor to perform declarations, initializations, and parsing command line, as shown below.

```
// Copyright 2002
// Michael van Dam, Rebecca Shafee, Jim Brody, Steve Quake.
// Department of Applied Physics
// California Institute of Technology
//
// Heavily modified from an original version by jpbrody and quake.
//
// make_pvalues:
// Compute pvalues for all pairs of UniGene clusters from their
// 'onebit' (discretized) expression data.
// Output file format:
//
// Line 1: make_pvalues (program name)
// Line 2: 3.0 (version number)
// Line 3: Hs (organism)
// Line 4: 150 (unigene build)
// Line 5: 2 (expt group number)
// Line 6: 28063 (number of clusters with non-null 'onebit')
// Line 7: 43 (number of experiments in exptgroup)
// Line 8: -5 (threshold/cutoff p-value)
//
// Then the data: pvalue clust1 clust2 N dot dist (TAB-delimited)
//
// Data only stored if pvalue < cutoff.
// Version info
#define MAJOR_VERSION 3
#define MINOR_VERSION 0
// Include files
#include "common.h"
#include "local.h"
#include "mysql.h"
#include <stdio.h>
#include <stdlib.h>
#include <math.h>
#include <string>
// Compute the Fisher Exact Probability for a contingency table.
// http://www.netlib.or/toms/643
// Algorithm 643, Collected Algorithms from ACM.
// Published in Transactions on Mathematical Software 19(4): 484-488, 1993.
//
// fexact (nrow, ncol, table, ldtabl, expect, percnt, emin, prt, pre)
//
// nrow, ncol : integer
// ldtable : integer (leading dimension of 'table')
// table : double precision (nrow x ncol matrix)
// expect, percnt, emin, prt, pre : double precision
//
// Note, in Fortran, all arguments are 'passed-by-reference'.
// Also, arrays stored in order such that indices should be reversed; here
// doesn't matter
extern "C" void fexact_(int &nrow, int &ncol, double *table, int &ldtabl,
double &expect, double &percnt, double &emin, double &prt, double &pre,
double *fact);
// The Fisher exact probability for a contingency table is the summation
// of pvalues for all less-likely tables having the same margin totals.
//
// A less accurate, but still usable calculation is simply to take the
// p-value of the given table (no summation). For low p-values this tends
// to be quite accurate, but for higher p-values can be quite inaccurate.
// However, if we are only interested in the small fraction of pairs
// which have low-pvalues, then this provides a MUCH faster calculation.
float p_single(int N, int np, int nz, int nm, int mp, int mz, int mm,
```

-continued

```
        int kpp, int kpz, int kmz,
    int kzp, int kzm, int kpm,
    int kmp, int kmm, int kzz);
int status_interval = 100000;
double* f = NULL; // will store table of ln(n!)
// Error codes (see program for description)
#define ERROR_USAGE      -1
#define ERROR_DB_CONNECT -100
#define ERROR_FOPEN      -200
// Initialize mysql variables
MYSQL* dbc = NULL;
MYSQL_RES *result = NULL;   // pointer to a result
MYSQL_ROW row;
char query [1024];
int main (int argc, char **argv) {
    // -------------------
    // Parse command line
    // -------------------
    int nargs = 4+1;
    if (argc < nargs) {
        cout << endl;
        cout <<"Usage: make_pvalues <organism><exptgroup><cutoff><outputfile>" << endl;
        cout << endl;
        cout << "   <organism> is the two-letter organism code (e.g. Hs)" << endl;
        cout << "   <exptgroup> is the expt group id" << endl;
        cout << "   <cutoff> is the log of highest p-value to store" << endl;
        cout << "   <outputfile> is the name of the results file" << endl;
        exit (ERROR_USAGE);
    }
    char* organism = argv[1];
    int exptgroup;
    sscanf (argv[2], "%d", &exptgroup);
    float cutoff;
    sscanf (argv[3], "%f", &cutoff);
    char* outputfile = argv[4];
    // Summarize run parameters
    cout << "make_pvalues v" << MAJOR_VERSION << "." << MINOR_VERSION << endl;
    cout << "Organism: " << organism << endl;
    cout << "Exptgroup: " << exptgroup << endl;
    cout << "Cutoff:    " << cutoff << endl;
    cout << "Output file: " << outputfile << endl;
    int build = 150; // hardwired for now
    // Figure out MySQL table names
    char* table_onebit = new char [1024];
    sprintf (table_onebit, "%s%d_onebit", organism, build);
    char* table_exptgroups = "exptgroups";
```

Establishing Connection with Database and Importing Discretized Expression Ratios In this section, the computer code directs the processor to establish connection with database containing discretized expression ratios and import such ratios, as shown below.

```
// -----------------------------------------
// Establish connection with database (MySQL)
// -----------------------------------------
cout << "Connecting to database........";
// Attempt connection
MYSQL *dbh = mysql_init (NULL);
dbc = mysql_real_connect (dbh, DB_HOST, DB_USER, DB_PASS, PVAL_DB,
        DB_PORT, DB_SOCK, DB_FLAG);
if (mysql_errno(dbc)) {
    cout << endl;
    cout << "ERROR: couldn't connect to database server" << endl;
    cout << "MYSQL_ERROR:   " << mysql_error(dbc) << endl;
    exit (ERROR_DB_CONNECT);
}
cout << "Successful" << endl;
// -----------------------------------------
// Read in the onebit strings from the database
// -----------------------------------------
// first get the number of items so we know how big to make
// the arrays
ulong n_clusters = 0;
```

-continued

```
ulong n_expts = 0;
// SOMETIMES THE VALUE CAN BE NULL!!!!!
// COUNT counts only non-NULL records... we need to make sure
// to retrieve only non-NULL records later...
sprintf(query, "SELECT COUNT(group%d) FROM %s", exptgroup, table_onebit);
mysql_query (dbc,query);
result = mysql_store_result (dbc);
row = mysql_fetch_row (result);
sscanf (row[0], "%lu", &n_clusters);
mysql_free_result(result);
cout << "Found " << n_clusters << " clusters" << endl;
sprintf(query, "SELECT nexpts FROM %s WHERE id=%d", table_exptgroups,
exptgroup);
mysql_query (dbc,query);
result = mysql_store_result (dbc);
row = mysql_fetch_row (result);
sscanf (row[0], "%lu", &n_expts);
mysql_free_result(result);
cout << "Found " << n_expts << " experiments" << endl;
// Initialize arrays
cout << "Allocating memory for arrays...";
ulong* clusterid = new ulong [n_clusters];
char** onebitstring = new char* [n_clusters];
for (int i=0; i < n_clusters; i++) {
    onebitstring[i] = new char [n_expts];
    if (onebitstring[i] == NULL) {
        cout << "ERROR: could not allocate for onebitstring[" << i <<"]" << endl;
    }
}
cout << "Done" << endl;
cout << "Precomputing table of ln(n!)... ";
f = new double [n_expts+1];
f[0] = 0.0;
f[1] = 0.0;
f[2] = log(2.0);
for (int i=3; i <= n_expts; i += 2) {
    f[i] = f[i-1] + log(i);
    int j = i+1;
    if (j <= n_expts) {
        f[j] = f[i] + f[2] + f[j/2] - f[j/2-1];
    }
}
cout << "Done" << endl;
#define MINP 1000
ulong* histo = new ulong [MINP];
int i;
for (i=0; i<MINP; i++) histo[i] = 0;
// Read database into arrays
cout << "Reading database into arrays... ";
sprintf (query, "SELECT cluster,group%d FROM %s WHERE group%d IS NOT NULL",
exptgroup, table_onebit, exptgroup);
mysql_query (dbc,query);
result = mysql_store_result (dbc);
ulong temp_cluster;
for (int i=0; i < n_clusters; i++) {
    row = mysql_fetch_row (result);
    sscanf (row[0], "%lu", &temp_cluster);
    clusterid[i] = temp_cluster;
    if(row[1]) {
        //sscanf (row[1], "%s", temp_string);
        strncpy (onebitstring[i], row[1], n_expts);
    }
    else {
        onebitstring[i] = NULL;
    }
}
mysql_free_result(result);
cout << "Done" << endl;
```

Computing p-Values for Gene Pairs and Writing Output File.

In this section, the computer code directs the processor to compute p-values for gene pairs and write an output file. More specifically, the processor forms a co-expression table, calculate probabilities for gene correlations, and predicts gene relations as shown below.

```
// ------------------------------------------------------
// Compute p-values for gene pairs and write output file
// ------------------------------------------------------
// --------------------------
// Initialization for FEXACT
//
// We must pass actual variables to the FORTRAN subroutine since
// everything is passed by reference, never by value.
// --------------------------
int nrow = 3;
int ncol = 3;
int ldtabl = 3;
// Cochran conditions... if satisfied do chi-squared instead of
// Fisher (faster)
double expect = 5.0;
double percnt = 80.0;
double emin = 1.0;
double prt; // output
double pre; // output
double* table = new double [9];
float p;
int dotproduct;
// Create output file
cout << "Creating output file...";
FILE* ofile = fopen (outputfile, "w");
if (ofile == NULL) {
    cout << endl;
    cout << "ERROR: could not create output file";
    exit (ERROR_FOPEN);
}
cout << "Done" << endl;
// Write headers to output file
fprintf (ofile, "make_pvalues\n");
fprintf (ofile, "%d.%d\n", MAJOR_VERSION, MINOR_VERSION);
fprintf (ofile, "%s\n", organism);
fprintf (ofile, "%d\n", build);
fprintf (ofile, "%d\n", exptgroup);
fprintf (ofile, "%d\n", n_clusters);
fprintf (ofile, "%d\n", n_expts);
fprintf (ofile, "%f\n", cutoff);
// Main program loop
ulong pairs = 0;
ulong pairs_nodata = 0;
cout << "Writing output file..." << endl;
for (int i=0; i < n_clusters-1; i++) {
  for (int j=i+1; j < n_clusters; j++) {
    pairs++;
    // These need to be reset every time
    int N=0;
    int np=0, nz=0, nm=0;
    int mp=0, mz=0, mm=0;
    int kpp=0, kpz=0, kpm=0, kzp=0, kzz=0, kzm=0, kmp=0, kmz=0, kmm=0;
    int dotproduct = 0;
    int distsquared = 0;
    if (onebitstring[i] && onebitstring[j]) {
        for (int x=0; x < n_expts; x++) {
        //char* chars = substr(onebitstring[i],x,1). substr(onebitstring[j],x,1);
        char char1 = onebitstring[i][x];
        char char2 = onebitstring[j][x];
        if (char1 == '.' || char2 == '.') {
          // do nothing
        }
        else if (char1 == '+' && char2 == '+') {kpp++; dotproduct ++; }
        else if (char1 == '+' && char2 == '0') {kpz++; distsquared += 1; }
        else if (char1 == '+' && char2 == '-') {kpm++; dotproduct --; distsquared += 4; }
        else if (char1 == '0' && char2 == '+') {kzp++; distsquared += 1; }
        else if (char1 == '0' && char2 == '0') {kzz++; }
        else if (char1 == '0' && char2 == '-') {kzm++; distsquared += 1; }
        else if (char1 == '-' && char2 == '+') {kmp++; dotproduct --; distsquared += 4; }
        else if (char1 == '-' && char2 == '0') {kmz++; distsquared += 1; }
        else if (char1 == '-' && char2 =='-') {kmm++; dotproduct ++; }
        else {
          // error
        }
```

-continued

```
        // Count statistics
        // The coincidences are indicated by k[mzp][mzp]
        // (m-minus,z-zero,p-plus) and the counts by m[mp]and n[mp].
        //
        //              j
        //
        //         kpp kpz kpm np
        //      i  kzp kzz kzm nz
        //         kmp kmz kmm nm
        //
        //         mp  mz  mm  N
        } // endfor: x
    } // endif: onebitstrings both defined
    else {
      pairs_nodata ++;
      continue; // skip iteration if no data
    }
    np = kpp + kpz + kpm;
    nz = kzp + kzz + kzm;
    nm = kmp + kmz + kmm;
    mp = kpp + kzp + kmp;
    mz = kpz + kzz + kmz;
    mm = kpm + kzm + kmm;
    N = np + nz + nm;
    if (N == 0) {
      // No data – jump to next iteration
      // fexact terminates on this condition
      pairs_nodata ++;
      continue;
    }
    else if (N == 1) {
      // fexact crashes... therefore set p manually
      p = 0.0;
    }
    else { // N > 1
    // Load values into table for fexact...
    table[0] = kpp;
    table[1] = kzp;
    table[2] = kmp;
    table[3] = kpz;
    table[4] = kzz;
    table[5] = kmz;
    table[6] = kpm;
    table[7] = kzm;
    table[8] = kmm;
    fexact_(nrow, ncol, table, ldtabl, expect, percnt, emin, prt, pre, f);
    p = log10(pre);
    // float p_old = p_single (N,np,nz,nm,mp,mz,mm,
    //       kpp,kpz,kmz,kzp,kzm,kpm,kmp,kmm,kzz)/2.30258;
    // NOTE: ln(10)=2.30258
    } // endif
    // Output to file if meets cutoff
    if (p <= cutoff) {
        fprintf (ofile, "%f\t%lu\t%lu\t%d\t%d\t%d\n", p, clusterid[i], clusterid[j], N, dotproduct,
distsquared);
    }
    if (!(pairs % status_interval)) {
        cout << "Done "<< pairs <<" pairs (" << pairs_nodata <<" no data)" <<endl;
    }
    // Update histogram of p-values
    if (p > 0) {
        if (p > 1.0e-6) printf ("p %f> 0, adding to 0:-1 bin\n", p);
        p = 0;
    }
    if (p <= -MINP) {
        printf ("p %f< -MINP, adding to MINP-1:MINP bin\n", p);
        p = -MINP+1;
    }
    histo[int(-p)]++;
    } // endfor: i
} // endfor: j
fclose(ofile);
cout <<"end"<<endl;
cout << endl;
cout << "Final total pairs:" << pairs << endl;
cout << "Final total nodata:" << pairs_nodata << endl;
cout << endl;
cout << "Writing histogram..." << endl;
cout << "Bin Count" << endl;
for (i=0; i<MINP; i++) {
```

-continued

```
cout << -i << ":" << -(i+1) << " " << histo[i] << endl;
    }
}
float p_single(int N, int np, int nz, int nm, int mp, int mz, int mm, int kpp, int kpz, int kmz, int
kzp, int kzm, int kpm,\
        int kmp, int kmm, int kzz) {
// Can probably squeeze out a little more efficiency by passing
// fewer parameters (some can be deduced from the others as only
// 9 are independent)
return f[np] + f[nz] + f[nm] + f[mp] + f[mz] + f[mm] - f[N]
        - f[kpp] - f[kpz] - f[kpm]
        - f[kzp] - f[kzz] - f[kzm]
    - f[kmp] - f[kmz] - f[kmm];
}
```

It is understood the examples and embodiments described herein are for illustrative purposes only and that various modifications or changes in light thereof will be suggested to persons skilled in the art and are to be included within the spirit and purview of this application and scope of the appended claims.

What is claimed is:

1. A method for predicting gene relationships comprising:

providing a control sample and a plurality of experimental samples;

performing one experiment on each of the plurality of experimental samples;

measuring a first gene control signal corresponding to a first gene from the control sample;

measuring a first gene experimental signal corresponding to the first gene from each of the plurality of experimental samples;

calculating a first expression ratio corresponding to the first gene for each of the plurality of experimental samples;

discretizing the first expression ratio for each of the plurality of experimental samples into one of three indications, where the three indications representing the first gene up-regulated, not changed, or down-regulated;

measuring a second gene control signal corresponding to a second gene from the control samples;

measuring a second gene experimental signal corresponding to the second gene from each of the plurality of experimental samples;

calculating a second expression ratio corresponding to the second gene for each of the plurality of experimental samples;

discretizing the second expression ratio for each of the plurality of experimental samples into one of the three indications, where the three indications representing the second gene up-regulated, not changed, or down-regulated;

calculating the probability that the combination of the discretized first expression ratio for each of the plurality of experimental samples and the discretized second expression ratio for each of the plurality of experimental samples arises by random chance; and determining whether the first gene and the second gene are related.

2. The method of claim 1 for predicting gene relationships further comprising:

measuring a first background control signal corresponding to the first gene from the control sample;

measuring a first background experimental signal corresponding to the first gene from each of the plurality of experimental samples;

measuring a second background control signal corresponding to the second gene from the control sample; and measuring a second background experimental signal corresponding to the second gene from each of the plurality of experimental samples.

3. The method of claim 1 wherein the measuring a first gene control signal corresponding to a first gene from the control sample comprising:

producing a plurality of mRNA control samples from the control sample;

producing a plurality of cDNA control samples from the plurality of mRNA control samples;

placing the plurality of cDNA control samples onto a microarray to hybridize with one or a plurality of probes for the first gene; and measuring the first gene control signal resulting from the hybridization.

4. The method of claim 1 wherein the measuring a first gene experimental signal corresponding to the first gene from each of the plurality of experimental samples comprising:

producing a plurality of mRNA experimental samples from each of the plurality of experimental samples;

producing a plurality of cDNA experimental samples from the plurality of mRNA experimental samples;

placing the plurality of cDNA experimental samples onto a plurality of microarrays to hybridize with a plurality of probes for the first gene; and measuring the first gene experimental signal resulting from each hybridization.

5. The method of claim 1 wherein the discretizing the first expression ratio for each of the plurality of experimental samples into one of three indications comprising:

if the first expression ratio is larger than a first noise threshold, assigning the first expression ratio to be a first indication representing the first gene up-regulated;

if the first expression ratio is smaller than or equal to the first noise threshold and larger than or equal to a second noise threshold, assigning the first expression ratio to be a second indication representing the first gene not changed; and if the first expression ratio is smaller than the second noise threshold, assigning the first expression ratio to be a third indication representing the first gene as down-regulated.

6. The method of claim 1 wherein the discretizing the second expression ratio for each of the plurality of experimental samples into one of the three indications comprising:

if the second expression ratio is larger than a first noise threshold, assigning the second expression ratio to be a first indication representing the second gene up-regulated;

if the second expression ratio is smaller than or equal to the first noise threshold and larger than or equal to a second noise threshold, assigning the second expression ratio to be a second indication representing the second gene not changed; and if the second expression ratio is smaller than the second noise threshold, assigning the second expression ratio to be a third indication representing the second gene as down-regulated.

7. The method of claim 1 wherein the calculating a probability is accomplished with the Fisher Exact test for 3 by 3 contingency tables.

8. The method of claim 1 wherein the calculating a probability is accomplished with the approximated Fisher Exact test.

9. The method of claim 1 wherein the determining whether the first gene and the second gene are related comprising:

if the probability is smaller than a correlation factor, concluding the first gene and the second gene as related; and if the probability is larger than or equal to the correlation factor, concluding the first gene and the second gene as unrelated.

10. The method of claim 1 for predicting gene relationships further comprising if the first gene and the second gene are related, storing their relation into a gene correlation database.

11. The method of claim 2 the measuring a first background control signal corresponding to the first gene from the control sample comprising:

producing a plurality of mRNA control samples from the control sample;

producing a plurality of cDNA control samples from the plurality of mRNA control samples;

placing the plurality of cDNA control samples onto a plurality of microarrays to hybridize with one or a plurality of probes for the first gene; and measuring the first background control signal resulting from each hybridization.

12. The method of claim 2 wherein the measuring a first background experimental signal corresponding to the first gene from each of the plurality of experimental samples comprising:

producing a plurality of mRNA experimental samples from each of the plurality of experimental samples;

producing a plurality of cDNA experimental samples from the plurality of mRNA experimental samples;

placing the plurality of cDNA experimental samples onto a microarray to hybridize with a plurality of probes for the first gene; and measuring the first background experimental signal resulting from the hybridization.

13. The method of claim 2 wherein the calculating a first expression ratio corresponding to the first gene for each of the plurality of experimental samples comprising:

calculating a first experimental difference by subtracting the first background experimental signal from the first gene experimental signal for the each of the plurality of experimental samples;

calculating a first control difference by subtracting the first background control signal from the first gene control signal; and calculating the first expression ratio,of the first experimental difference to the first control difference.

14. The method of claim 2 wherein the calculating a second expression ratio corresponding to the second gene for each of the plurality of experimental samples comprising:

calculating a second experimental difference by subtracting the second background experimental signal from the second gene experimental signal for the each of the plurality of experimental samples;

calculating a second control difference by subtracting the second background control signal from the second gene control signal; and calculating the second expression ratio of the second experimental difference to the second control difference.

15. A method for processing gene expression ratios comprising:

gathering gene expression data, the gene expression data comprising a first expression ratio for a first gene for each of a plurality of experiments and a second expression ratio for a second gene for each of the plurality of experiments;

discretizing the first expression ratio for each of the plurality of experiments into one of three indications, the three indications representing the first gene up-regulated, not changed, or down-regulated;

discretizing the second expression ratio for each of the plurality of experiments into one of three indications, the three indications representing the second gene up-regulated, not changed, or down-regulated;

calculating the probability that the combination of the discretized first expression ratio for each of the plurality of experiments and the discretized second expression ratio for each of the plurality of experiments arises by random chance; and determining whether the first gene and the second gene are related.

16. The method of claim 15 for processing gene expression ratios further comprising:

if the first gene and the second gene are related, storing their relation into a gene correlation database.

17. The method of claim 15 wherein the discretizing the first expression ratio for each of the plurality of experiments into one of three indications comprising:

if the first expression ratio is larger than a first noise threshold, assigning the first expression ratio to be a first indication representing the first gene up-regulated;

if the first expression ratio is smaller than or equal to the first noise threshold and larger than or equal to a second noise threshold, assigning the first expression ratio to be a second indication representing the first gene not changed; and if the first expression ratio is smaller than the second noise threshold, assigning the first expression ratio to be a third indication representing the first gene as down-regulated.

18. The method of claim 16 wherein the discretizing the second expression ratio for each of the plurality of experiments into one of three indications comprising:

if the second expression ratio is larger than a first noise threshold, assigning the second expression ratio to be a first indication representing the second gene up-regulated;

if the second expression ratio is smaller than or equal to the first noise threshold and larger than or equal to a second noise threshold, assigning the second expression ratio to be a second indication representing the second gene not changed; and if the second expression ratio is smaller than the second noise threshold, assigning the second expression ratio to be a third indication representing the second gene as down-regulated.

19. The method of claim 15 wherein the calculating a probability is accomplished with the Fisher Exact test for 3 by 3 contingency tables.

20. The method of claim 15 wherein the calculating a probability is accomplished with the approximated Fisher Exact test.

21. The method of claim 15 wherein the determining whether the first gene and the second gene are related comprising:

if the probability is smaller than a correlation factor, concluding the first gene and the second gene as related; and if the probability is larger than or equal to the correlation factor, concluding the first gene and the second gene as unrelated.

22. A method for processing gene expression ratios comprising:

gathering gene expression data, the gene expression data comprising a first gene control signal and a first gene experimental signal for a first gene for each of a plurality of experiments, and a second gene control signal and a second gene experimental signal for a second gene for each of the plurality of experiments;

discretizing the first expression ratio for each of the plurality of experiments into one of three indications, the three indications representing the first gene up-regulated, not changed, or down-regulated;

discretizing the second expression ratio for each of the plurality of experiments into one of three indications, the three indications representing the second gene up-regulated, not changed, or down-regulated;

calculating the probability that the combination of the discretized first expression ratio for each of the plurality of experiments and the discretized second expression ratio for each of the plurality of experiments arises by random chance; and determining whether the first gene and the second gene are related.

23. A computer-readable medium including instructions for processing gene expression ratios comprising:

one or more instructions for gathering gene expression data, the gene expression data comprising a first expression ratio for a first gene for each of a plurality of experiments and a second expression ratio for a second gene for each of the plurality of experiments;

one or more instructions for discretizing the first expression ratio for each of the plurality of experiments into one of three indications, the three indications representing the first gene up-regulated, not changed, or down-regulated;

one or more instructions for discretizing the second expression ratio for each of the plurality of experiments into one of three indications, the three indications representing the second gene up-regulated, not changed, or down-regulated;

one or more instructions for calculating the probability that the combination of the discretized first expression ratio for each of the plurality of experiments and the discretized second expression ratio for each of the plurality of experiments arises by random chance; and one or more instructions for determining whether the first gene and the second gene are related.

* * * * *

UNITED STATES PATENT AND TRADEMARK OFFICE
CERTIFICATE OF CORRECTION

PATENT NO. : 6,947,846 B2 Page 1 of 1
DATED : September 20, 2005
INVENTOR(S) : Stephen R. Quake et al.

It is certified that error appears in the above-identified patent and that said Letters Patent is hereby corrected as shown below:

<u>Column 1,</u>
Line 15, change "Not Applicable" to -- Work described herein has been supported, at least in part, by Grant No. HG 00047-02 awarded by the National Institutes of Health. The United States Government may therefore have certain rights in the invention. --.

Signed and Sealed this

Eleventh Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,947,846 B2 | Page 1 of 1 |
| APPLICATION NO. | : 10/289141 | |
| DATED | : September 20, 2005 | |
| INVENTOR(S) | : Stephen R. Quake et al. | |

It is certified that error appears in the above-identified patent and that said Letters Patent is hereby corrected as shown below:

In the specification

In col. 1, line 15 change "Not Applicable" to --"This invention was made with government support under Grant No. HG000047 awarded by the National Institutes of Health. The government has certain rights in the invention."

Signed and Sealed this
Twentieth Day of October, 2015

Michelle K. Lee
*Director of the United States Patent and Trademark Office*